United States Patent
Oi et al.

(10) Patent No.: US 8,066,750 B2
(45) Date of Patent: Nov. 29, 2011

(54) PORT STRUCTURES FOR NON-RIGID BONE PLATES

(75) Inventors: Nelson Oi, Memphis, TN (US); Wilder Companioni, Cordova, TN (US); Jason Michael May, Cordova, TN (US); Michael V. West, Somerville, TN (US); Stephen Edward White, Germantown, TN (US)

(73) Assignee: Warsaw Orthopedic, Inc, Warsaw, IN (US)

( * ) Notice: Subject to any disclaimer, the term of this patent is extended or adjusted under 35 U.S.C. 154(b) by 1236 days.

(21) Appl. No.: 11/544,839

(22) Filed: Oct. 6, 2006

(65) Prior Publication Data
US 2008/0083613 A1 Apr. 10, 2008

(51) Int. Cl.
*A61B 17/80* (2006.01)
(52) U.S. Cl. .................................................. 606/289
(58) Field of Classification Search .......... 606/280–296, 606/902–906
See application file for complete search history.

(56) References Cited

U.S. PATENT DOCUMENTS

| | | | |
|---|---|---|---|
| 2,677,369 A | 5/1954 | Knowles | |
| 3,463,158 A | 8/1969 | Schmitt et al. | |
| 3,710,789 A | 1/1973 | Ersek | |
| 3,848,601 A | 11/1974 | Ma et al. | |
| 3,867,728 A | 2/1975 | Stubstad et al. | |
| 3,875,595 A | 4/1975 | Froning | |
| 3,876,728 A | 4/1975 | Kuroda et al. | |
| 4,089,071 A | 5/1978 | Kalnberz et al. | |
| 4,179,810 A | 12/1979 | Kirsch | |
| 4,309,777 A | 1/1982 | Patil | |
| 4,349,921 A | 9/1982 | Kuntz | |
| 4,428,082 A | 1/1984 | Naficy | |
| 4,454,612 A | 6/1984 | McDaniel et al. | |
| 4,599,086 A | 7/1986 | Doty | |
| 4,663,358 A | 5/1987 | Hyon et al. | |
| 4,697,582 A | 10/1987 | William | |
| 4,714,469 A | 12/1987 | Kenna | |
| 4,743,256 A | 5/1988 | Brantigan | |
| 4,743,260 A | 5/1988 | Burton | |
| 4,759,769 A | 7/1988 | Hedman et al. | |
| 4,772,287 A | 9/1988 | Ray et al. | |
| 4,863,476 A | 9/1989 | Shepperd | |
| 4,863,477 A | 9/1989 | Monson | |
| 4,874,389 A | 10/1989 | Downey | |
| 4,887,595 A | 12/1989 | Heinig et al. | |
| 4,904,260 A | 2/1990 | Ray et al. | |

(Continued)

FOREIGN PATENT DOCUMENTS

DE 2263842 7/1974

(Continued)

OTHER PUBLICATIONS

Rodgers, et al., Single-Level Instrumented ACDF Using an Embroidered Anterior Plate (Embrace-C), Spine Midwest, Jefferson City, MO, Mar. 11, 2009, 2 pages.

(Continued)

*Primary Examiner* — Thomas C. Barrett
*Assistant Examiner* — Sameh Boles (57) ABSTRACT

There is provided an orthopedic plate and port structures for the plate. The plate can be non-rigid and includes at least one hole for receiving an anchor or an anchor retaining device. The at least one hole can include a rigid port structure that prevents or resists deformation of the plate when the anchor or anchor retaining device is engaged thereto.

31 Claims, 8 Drawing Sheets

U.S. PATENT DOCUMENTS

| | | | |
|---|---|---|---|
| 4,904,261 A | 2/1990 | Dove et al. |
| 4,911,718 A | 3/1990 | Lee et al. |
| 4,917,704 A | 4/1990 | Frey et al. |
| 4,932,969 A | 6/1990 | Frey et al. |
| 4,932,975 A | 6/1990 | Main et al. |
| 4,946,378 A | 8/1990 | Hirayama et al. |
| 4,955,908 A | 9/1990 | Frey et al. |
| 4,978,355 A | 12/1990 | Frey et al. |
| 5,002,576 A | 3/1991 | Fuhrmann et al. |
| 5,011,484 A | 4/1991 | Bréard |
| 5,013,316 A | 5/1991 | Goble et al. |
| 5,015,247 A | 5/1991 | Michelson |
| 5,015,255 A | 5/1991 | Kuslich |
| 5,035,716 A | 7/1991 | Downey |
| 5,047,055 A | 9/1991 | Bao et al. |
| 5,053,049 A | 10/1991 | Campbell |
| 5,055,104 A | 10/1991 | Ray |
| 5,057,111 A | 10/1991 | Park |
| 5,059,193 A | 10/1991 | Kuslich |
| 5,071,437 A | 12/1991 | Steffee |
| 5,092,866 A | 3/1992 | Breard et al. |
| 5,108,395 A | 4/1992 | Laurain |
| 5,108,397 A | 4/1992 | White |
| 5,108,438 A | 4/1992 | Stone |
| 5,123,926 A | 6/1992 | Pisharodi |
| 5,147,646 A | 9/1992 | Graham |
| 5,171,281 A | 12/1992 | Parsons et al. |
| 5,176,708 A | 1/1993 | Frey et al. |
| 5,192,326 A | 3/1993 | Bao et al. |
| 5,192,327 A | 3/1993 | Brantigan |
| 5,234,431 A | 8/1993 | Keller |
| 5,236,460 A | 8/1993 | Barber |
| 5,261,911 A | 11/1993 | Carl |
| 5,263,953 A | 11/1993 | Bagby |
| 5,306,307 A | 4/1994 | Senter et al. |
| 5,306,308 A | 4/1994 | Gross et al. |
| 5,314,478 A | 5/1994 | Oka et al. |
| 5,320,644 A | 6/1994 | Baumgartner |
| 5,346,492 A | 9/1994 | Morgan |
| 5,370,697 A | 12/1994 | Baumgartner |
| 5,380,328 A | 1/1995 | Morgan |
| 5,390,683 A | 2/1995 | Pisharodi |
| 5,423,816 A | 6/1995 | Lin |
| 5,425,772 A | 6/1995 | Brantigan |
| 5,431,658 A | 7/1995 | Moskovich |
| 5,443,483 A | 8/1995 | Kirsch |
| 5,443,514 A | 8/1995 | Steffee |
| 5,443,727 A | 8/1995 | Gagnon |
| 5,458,638 A | 10/1995 | Kuslich et al. |
| 5,458,642 A | 10/1995 | Beer et al. |
| 5,489,307 A | 2/1996 | Kuslich et al. |
| 5,496,318 A | 3/1996 | Howland et al. |
| 5,514,180 A | 5/1996 | Heggeness et al. |
| 5,534,028 A | 7/1996 | Bao et al. |
| 5,545,229 A | 8/1996 | Parsons et al. |
| 5,549,679 A | 8/1996 | Kuslich |
| 5,554,191 A | 9/1996 | Lahille et al. |
| 5,562,736 A | 10/1996 | Ray et al. |
| 5,571,189 A | 11/1996 | Kuslich |
| 5,578,034 A * | 11/1996 | Estes ............................ 606/281 |
| 5,609,636 A | 3/1997 | Kohrs et al. |
| 5,634,945 A | 6/1997 | Pernia et al. |
| 5,643,261 A | 7/1997 | Schäfer et al. |
| 5,645,597 A | 7/1997 | Krapiva |
| 5,645,598 A | 7/1997 | Brosnahan, III |
| 5,645,599 A | 7/1997 | Samani |
| 5,674,294 A | 10/1997 | Bainville et al. |
| 5,674,295 A | 10/1997 | Ray et al. |
| 5,674,296 A | 10/1997 | Bryan et al. |
| 5,676,702 A | 10/1997 | Ratron |
| 5,681,310 A | 10/1997 | Yuan et al. |
| 5,681,311 A | 10/1997 | Foley et al. |
| 5,702,450 A | 12/1997 | Bisserie |
| 5,704,936 A | 1/1998 | Mazel |
| 5,716,416 A | 2/1998 | Lin |
| 5,720,746 A | 2/1998 | Soubeiran |
| 5,725,582 A | 3/1998 | Bevan et al. |
| 5,741,253 A | 4/1998 | Michelson |
| 5,749,916 A | 5/1998 | Richelsoph |
| 5,755,796 A | 5/1998 | Ibo et al. |
| 5,785,710 A | 7/1998 | Michelson |
| 5,797,909 A | 8/1998 | Michelson |
| 5,824,093 A | 10/1998 | Ray et al. |
| 5,824,094 A | 10/1998 | Serhan et al. |
| 5,827,328 A | 10/1998 | Buttermann |
| 5,863,551 A | 1/1999 | Woerly |
| 5,865,846 A | 2/1999 | Bryan et al. |
| 5,865,848 A | 2/1999 | Baker |
| 5,888,226 A | 3/1999 | Rogozinski |
| 5,893,889 A | 4/1999 | Harrington |
| 5,899,908 A | 5/1999 | Kuslich et al. |
| 5,904,683 A | 5/1999 | Pohndorf et al. |
| RE36,221 E | 6/1999 | Breard et al. |
| 5,928,284 A | 7/1999 | Mehdizadeh |
| 5,954,722 A | 9/1999 | Bono |
| 5,976,186 A | 11/1999 | Bao et al. |
| 5,976,187 A | 11/1999 | Richelsoph |
| 5,984,967 A | 11/1999 | Zdeblick et al. |
| 5,989,291 A | 11/1999 | Ralph et al. |
| 6,001,130 A | 12/1999 | Bryan et al. |
| 6,019,793 A | 2/2000 | Perren et al. |
| 6,022,376 A | 2/2000 | Assell et al. |
| 6,045,552 A | 4/2000 | Zucherman et al. |
| 6,045,579 A | 4/2000 | Hochshuler et al. |
| 6,051,001 A | 4/2000 | Borghi |
| 6,059,829 A | 5/2000 | Schläpfer et al. |
| 6,063,121 A | 5/2000 | Xavier et al. |
| 6,080,193 A | 6/2000 | Hochshuler et al. |
| 6,086,595 A | 7/2000 | Yonemura et al. |
| 6,090,112 A | 7/2000 | Zucherman et al. |
| 6,090,998 A | 7/2000 | Grooms et al. |
| 6,093,205 A | 7/2000 | McLeod et al. |
| 6,096,080 A | 8/2000 | Nicholson et al. |
| 6,099,565 A | 8/2000 | Sakura, Jr. |
| 6,102,950 A | 8/2000 | Vaccaro |
| 6,110,210 A | 8/2000 | Norton et al. |
| 6,113,639 A | 9/2000 | Ray et al. |
| 6,120,503 A | 9/2000 | Michelson |
| 6,132,465 A | 10/2000 | Ray et al. |
| 6,139,579 A | 10/2000 | Steffee et al. |
| 6,152,927 A | 11/2000 | Farris et al. |
| 6,156,067 A | 12/2000 | Bryan et al. |
| 6,162,252 A | 12/2000 | Kuras et al. |
| 6,165,218 A | 12/2000 | Husson et al. |
| 6,176,881 B1 | 1/2001 | Schär et al. |
| 6,179,873 B1 | 1/2001 | Zientek |
| 6,179,874 B1 | 1/2001 | Cauthen |
| 6,183,471 B1 | 2/2001 | Zucherman et al. |
| 6,190,387 B1 | 2/2001 | Zucherman et al. |
| 6,190,413 B1 | 2/2001 | Sutcliffe |
| 6,193,757 B1 | 2/2001 | Foley et al. |
| 6,206,882 B1 | 3/2001 | Cohen |
| 6,206,923 B1 | 3/2001 | Boyd et al. |
| 6,221,109 B1 | 4/2001 | Geistlich et al. |
| 6,228,026 B1 | 5/2001 | Rullo et al. |
| 6,231,609 B1 | 5/2001 | Mehdizadeh |
| 6,241,769 B1 | 6/2001 | Nicholson et al. |
| 6,273,889 B1 | 8/2001 | Richelsoph |
| 6,296,644 B1 | 10/2001 | Saurat et al. |
| 6,296,665 B1 | 10/2001 | Strnad et al. |
| 6,312,431 B1 | 11/2001 | Asfora |
| 6,336,930 B1 | 1/2002 | Stalcup et al. |
| 6,348,071 B1 | 2/2002 | Steffee et al. |
| 6,395,032 B1 | 5/2002 | Gauchet |
| 6,395,034 B1 | 5/2002 | Suddaby |
| 6,402,784 B1 | 6/2002 | Wardlaw |
| 6,419,704 B1 | 7/2002 | Ferree |
| 6,425,919 B1 | 7/2002 | Lambrecht |
| 6,447,512 B1 | 9/2002 | Landry et al. |
| 6,475,219 B1 | 11/2002 | Shelokov |
| 6,478,796 B2 | 11/2002 | Zucherman et al. |
| 6,482,234 B1 | 11/2002 | Weber et al. |
| 6,524,312 B2 | 2/2003 | Landry et al. |
| 6,565,571 B1 | 5/2003 | Jackowski et al. |
| 6,572,617 B1 | 6/2003 | Senegas |
| 6,575,976 B2 | 6/2003 | Grafton |
| 6,575,979 B1 | 6/2003 | Cragg |

| | | |
|---|---|---|
| 6,575,986 B2 | 6/2003 | Overaker |
| 6,579,321 B1 | 6/2003 | Gordon et al. |
| 6,582,433 B2 | 6/2003 | Yun |
| 6,582,466 B1 | 6/2003 | Gauchet |
| 6,582,468 B1 | 6/2003 | Gauchet |
| 6,585,769 B1 | 7/2003 | Muhanna et al. |
| 6,605,090 B1 | 8/2003 | Trieu et al. |
| 6,607,530 B1 | 8/2003 | Carl et al. |
| 6,610,093 B1 | 8/2003 | Pisharodi |
| 6,620,196 B1 | 9/2003 | Trieu |
| 6,645,211 B2 | 11/2003 | Magana |
| 6,645,248 B2 | 11/2003 | Casutt |
| 6,656,224 B2 | 12/2003 | Middleton |
| 6,669,732 B2 | 12/2003 | Serhan et al. |
| 6,679,883 B2 | 1/2004 | Hawkes et al. |
| 6,682,562 B2 | 1/2004 | Viart et al. |
| 6,699,246 B2 | 3/2004 | Zucherman et al. |
| 6,699,247 B2 | 3/2004 | Zucherman et al. |
| 6,706,067 B2 | 3/2004 | Shimp et al. |
| 6,719,796 B2 | 4/2004 | Cohen et al. |
| 6,726,721 B2 | 4/2004 | Stoy et al. |
| 6,733,531 B1 | 5/2004 | Trieu |
| 6,733,532 B1 | 5/2004 | Gauchet et al. |
| 6,733,533 B1 | 5/2004 | Lozier |
| 6,736,850 B2 | 5/2004 | Davis |
| 6,743,257 B2 | 6/2004 | Castro |
| 6,761,719 B2 | 7/2004 | Justis et al. |
| 6,764,514 B1 | 7/2004 | Li et al. |
| 6,773,460 B2 | 8/2004 | Jackson |
| 6,783,546 B2 | 8/2004 | Zucherman et al. |
| 6,793,658 B2 | 9/2004 | LeHuec et al. |
| 6,802,867 B2 | 10/2004 | Manasas et al. |
| 6,805,695 B2 | 10/2004 | Keith et al. |
| 6,805,697 B1 | 10/2004 | Helm et al. |
| 6,827,743 B2 | 12/2004 | Eisermann et al. |
| 6,830,589 B2 | 12/2004 | Erickson |
| 6,863,689 B2 | 3/2005 | Ralph et al. |
| 6,883,520 B2 | 4/2005 | Lambrecht et al. |
| 6,893,465 B2 | 5/2005 | Huang |
| 6,893,466 B2 | 5/2005 | Trieu |
| 6,899,713 B2 | 5/2005 | Shaolian et al. |
| 6,918,934 B2 | 7/2005 | Ralph et al. |
| 6,923,811 B1 | 8/2005 | Carl et al. |
| 6,923,820 B1 | 8/2005 | Nash et al. |
| 6,966,910 B2 | 11/2005 | Ritland |
| 6,979,353 B2 | 12/2005 | Bresina |
| 6,981,989 B1 | 1/2006 | Fleischmann et al. |
| 6,984,246 B2 | 1/2006 | Huang |
| 7,001,431 B2 | 2/2006 | Bao et al. |
| 7,022,122 B2 | 4/2006 | Amrein et al. |
| 7,022,138 B2 | 4/2006 | Mashburn |
| 7,029,498 B2 | 4/2006 | Boehm et al. |
| 7,052,515 B2 | 5/2006 | Simonson |
| 7,055,237 B2 | 6/2006 | Thomas |
| 7,056,577 B1 | 6/2006 | Bruce et al. |
| 7,060,097 B2 | 6/2006 | Fraser et al. |
| 7,074,240 B2 | 7/2006 | Pisharodi |
| 7,083,650 B2 | 8/2006 | Moskowitz et al. |
| 7,083,651 B2 | 8/2006 | Diaz et al. |
| 7,087,083 B2 | 8/2006 | Pasquet et al. |
| 7,112,222 B2 | 9/2006 | Fraser et al. |
| 7,112,223 B2 | 9/2006 | Davis |
| 7,115,129 B2 | 10/2006 | Heggeness |
| 7,115,142 B2 | 10/2006 | Muhanna et al. |
| 7,125,410 B2 | 10/2006 | Freudiger |
| 7,128,762 B2 | 10/2006 | Middleton |
| 7,153,325 B2 | 12/2006 | Kim et al. |
| 7,156,848 B2 | 1/2007 | Ferree |
| 7,156,877 B2 | 1/2007 | Lotz et al. |
| 7,163,558 B2 | 1/2007 | Senegas et al. |
| 7,166,130 B2 | 1/2007 | Ferree |
| 7,172,593 B2 | 2/2007 | Trieu et al. |
| 7,195,644 B2 | 3/2007 | Diaz et al. |
| 7,217,293 B2 | 5/2007 | Branch, Jr. |
| 7,220,282 B2 | 5/2007 | Kuslich |
| 7,238,204 B2 | 7/2007 | Le Couedic et al. |
| 7,255,699 B2 | 8/2007 | Paul |
| 7,255,714 B2 | 8/2007 | Malek |
| 7,267,687 B2 | 9/2007 | McGuckin, Jr. |
| 7,279,175 B2 | 10/2007 | Chen et al. |
| 7,282,063 B2 | 10/2007 | Cohen et al. |
| 7,303,583 B1 | 12/2007 | Schär et al. |
| 7,326,210 B2 | 2/2008 | Jahng et al. |
| 7,329,259 B2 | 2/2008 | Cragg |
| 7,335,205 B2 | 2/2008 | Aeschlimann et al. |
| 7,335,230 B2 | 2/2008 | Goulet et al. |
| 7,338,524 B2 | 3/2008 | Fell et al. |
| 7,338,525 B2 | 3/2008 | Ferree |
| 7,338,527 B2 | 3/2008 | Blatt et al. |
| 7,341,601 B2 | 3/2008 | Eisermann et al. |
| 7,347,872 B2 | 3/2008 | Goulet et al. |
| 7,393,351 B2 | 7/2008 | Woloszko et al. |
| 7,524,325 B2 * | 4/2009 | Khalili .................. 606/290 |
| 2002/0026244 A1 | 2/2002 | Trieu |
| 2002/0120270 A1 | 8/2002 | Trieu et al. |
| 2003/0023311 A1 | 1/2003 | Trieu |
| 2003/0187509 A1 | 10/2003 | Lemole, Jr. |
| 2003/0199984 A1 | 10/2003 | Trieu |
| 2004/0034375 A1 | 2/2004 | Ruiz et al. |
| 2004/0059418 A1 | 3/2004 | McKay et al. |
| 2004/0087949 A1 * | 5/2004 | Bono et al. .................. 606/61 |
| 2004/0097935 A1 | 5/2004 | Richelsoph et al. |
| 2004/0102779 A1 | 5/2004 | Nesper et al. |
| 2004/0116961 A1 | 6/2004 | Nesper et al. |
| 2004/0127904 A1 | 7/2004 | Konieczynski et al. |
| 2004/0127908 A1 | 7/2004 | Roman et al. |
| 2004/0210226 A1 | 10/2004 | Trieu |
| 2004/0210310 A1 | 10/2004 | Trieu |
| 2004/0215195 A1 * | 10/2004 | Shipp et al. .................. 606/69 |
| 2004/0254579 A1 | 12/2004 | Buhren et al. |
| 2004/0254644 A1 | 12/2004 | Taylor |
| 2005/0004574 A1 | 1/2005 | Muckter |
| 2005/0021032 A1 | 1/2005 | Koo |
| 2005/0033298 A1 | 2/2005 | Hawkes et al. |
| 2005/0125061 A1 | 6/2005 | Zucherman et al. |
| 2005/0147562 A1 | 7/2005 | Hunter et al. |
| 2005/0203626 A1 | 9/2005 | Sears et al. |
| 2005/0273105 A1 | 12/2005 | Konieczynski et al. |
| 2005/0277922 A1 | 12/2005 | Trieu et al. |
| 2005/0277937 A1 | 12/2005 | Leung et al. |
| 2005/0278029 A1 | 12/2005 | Trieu |
| 2006/0015104 A1 | 1/2006 | Dalton |
| 2006/0058881 A1 | 3/2006 | Trieu |
| 2006/0064171 A1 | 3/2006 | Trieu |
| 2006/0064172 A1 | 3/2006 | Trieu |
| 2006/0129154 A1 | 6/2006 | Shipp |
| 2007/0239158 A1 | 10/2007 | Trieu et al. |
| 2008/0015697 A1 | 1/2008 | McLeod et al. |
| 2008/0083613 A1 | 4/2008 | Oi et al. |
| 2008/0154376 A1 | 6/2008 | Bergeron |
| 2008/0173223 A1 | 7/2008 | Butcher et al. |
| 2008/0234753 A1 | 9/2008 | Trieu |

FOREIGN PATENT DOCUMENTS

| | | |
|---|---|---|
| DE | 2804936 A1 | 8/1979 |
| DE | 3023353 C2 | 4/1981 |
| DE | 3741493 A1 | 6/1989 |
| DE | 9000094.3 U1 | 4/1990 |
| DE | 19710392 C1 | 7/1999 |
| DE | 1306057 | 5/2003 |
| EP | 0077159 A1 | 4/1983 |
| EP | 0176728 B1 | 4/1986 |
| EP | 0560140 A1 | 9/1993 |
| EP | 0621020 A1 | 10/1994 |
| EP | 0700671 A1 | 3/1996 |
| EP | 0732093 B1 | 9/1996 |
| EP | 0880938 B1 | 12/1998 |
| FR | 2712486 A1 | 5/1995 |
| FR | 2744011 | 8/1997 |
| FR | 2769827 A1 | 4/1999 |
| SU | 895433 | 1/1982 |
| SU | 1560184 | 4/1990 |
| WO | WO9011740 A1 | 10/1990 |
| WO | WO9601598 A1 | 1/1996 |
| WO | WO9627345 A2 | 9/1996 |
| WO | WO9726817 A1 | 7/1997 |
| WO | WO9726847 A1 | 7/1997 |
| WO | WO9804217 A1 | 2/1998 |

| | | |
|---|---|---|
| WO | WO9959481 A1 | 11/1999 |
| WO | WO0004839 A1 | 2/2000 |
| WO | WO0004851 A1 | 2/2000 |
| WO | WO0013619 A1 | 3/2000 |
| WO | WO0013620 A1 | 3/2000 |
| WO | WO0059412 A1 | 10/2000 |
| WO | WO0061037 A1 | 10/2000 |
| WO | WO0106962 A1 | 2/2001 |
| WO | WO0145577 A2 | 6/2001 |
| WO | WO0217824 A2 | 3/2002 |
| WO | WO0234169 A2 | 5/2002 |
| WO | WO02067793 A2 | 9/2002 |
| WO | WO02078574 A1 | 10/2002 |
| WO | WO02091909 A2 | 11/2002 |
| WO | WO2006135770 A2 | 12/2006 |
| WO | WO2008100685 A8 | 8/2008 |

OTHER PUBLICATIONS

U.S. Appl. No. 12/059,501, filed Mar. 31, 2008.
Surgical Technique Using Bone Dowel Instrumentation for Anterior Approach, pp. 1-19, Sofamor Danek USA.
Reduced Profile Instrumentation, "Surgical Technique", J. Kenneth Burkus, M.D., John D. Dorchak, M.D., pp. 1-24, Sofamor Danek USA (1999).
U.S. Appl. No. 10/948,485, filed Sep. 23, 2004, 51 pages.
U.S. Appl. No. 10/948,659, filed Sep. 23, 2004, 51 pages.
U.S. Appl. No. 11/030,337, filed Jan. 6, 2005, 87 pages.
U.S. Appl. No. 11/178,945, filed Jul. 11, 2005, 100 pages.
U.S. Appl. No. 11/694,056, filed Mar. 30, 2007, 117 pages.
Brain, et al., "The Neurological Manifestations of Cervical Spondylosis", Brain: A Journal of Neurology, vol. 75; Macmillan & Co.; 1952; pp. 187-225.
Buttner-Janz, et al.; "Biomechanics of the SB Charite Lumbar Intervertebral Disc Endoprosthesis"; International Orthopedics; vol. 13; 1989; pp. 173-176.
Edeland; "Some Additional Suggestions for an Intervertebral Disc Prosthesis"; Dept. of Occupational Health; Vdvo PV AB; S-40508; Goteborg; Sweden; 1985 Butterworth & Co. Publishers Ltd.
Enker et al.; "Artificial Disc Replacement"; Spine; vol. 18; No. 8; 1993; pp. 1061-1070.
Hawkins, et al.; "Shear Stability of an Elastomeric Disc Spacer Within an Interbertebral Joint: A Parametric Study"; Journal of Biomechanical Engineering Technical Briefs; vol. 114; Aug. 1992; pp. 414-415.
Lee, et al.; "Development of a Prosthetic Intervertebral Disc"; Spine; vol. 16; No. 6; 1991; pp. S253-S255.
Ray; "The Artificial Disc-Introduction, History and Socioeconomics"; Clinical Efficacy and Outcome in the Diagnosis and Treatment of Low Back Pain; Raven Press, Ltd., NY; 1992; pp. 205-280.
Robinson et al.; "The Results of Anterior Interbody Fusion of the Cervical Spine"; The Journal of Bone & Joint Surgery; vol. 44-A, No. 8, Dec. 1962; pp. 1569-1587.
Morphology of the Human Skeleton, pp. 268270; 283-291; 315-331; 489-495.
Bryan Total Cervical Disc Prosthesis, Single Level Surgical Technique Manual, SPINALdynamics Corporation, 2000, 01080-004, pp. 29.
International Search Report—PCT/US01/24791.
International Search Report, PCT/US2007/080162, May 29, 2008.

* cited by examiner

PORT STRUCTURES FOR NON-RIGID BONE PLATES

BACKGROUND

The treatment of injuries to the spine includes the use of elongated rigid plates in the stabilization of the spine. Plating designs may allow for a uni-cortically or bi-cortically intrinsically stable implant. It has also been found that the plates can be useful in stabilizing the upper or lower cervical, thoracic, lumbar and/or sacral spine in traumatic, degenerative, tumorous or infectious processes. Moreover, these plates provide the additional benefit of allowing simultaneous neural decompression with immediate stability.

During the many years of development of spinal plating systems various needs have been recognized. For instance, the plate should provide stabilization that can control movement of each vertebral motion segment in six degrees of freedom and withstand axial loading of the spine. The plate should also be able to maintain stress levels below the endurance limits of the material while also providing a thickness that is small to lower its protrusion into the adjacent tissue along the spine. The anchors employed to connect the plate to the vertebrae should not loosen over time or back out from the plate. Many spinal plating systems have been developed in the last couple of decades that address some of the needs and requirements for spinal stabilization. Examples include those disclosed in U.S. Pat. No. 6,152,927 and U.S. Patent Application Publication No. 2004/0215195, each of which is incorporated herein by reference in its entirety.

Plates made to provide a non-rigid stabilization construct are beneficial in that the plate can have a lower modulus as compared to plates that are made rigidly. Non-rigid stabilization constructs can also be made from non-metal materials and provide desirable imaging characteristics since certain metals can produce imaging artifacts and scatter, which hinder the inspection of bone growth when using conventional imaging via X-ray, CAT scanning, or MRI techniques. However, non-rigid plates should also be adapted to allow secure engagement of the bone anchors to the bone to secure the plate along the spinal column. Non-rigid plates can be damaged during installation by bone anchors passing through the plate holes, or by the bone anchors or any anchor retention devices deforming the plate when engaged to the plate. Furthermore, bone anchors and anchor retaining devices may be susceptible to loosening or backing out after engagement with the plate.

SUMMARY

The present invention provides a novel orthopedic plate and port structures for the plate. The plate can be made to provide a flexible or non-rigid body with at least one hole for receiving an anchor or an anchor retaining device. The at least one hole can include a more rigid or rigid port structure that prevents or resists deformation of the plate when the at least one anchor or anchor retaining device is engaged thereto.

In another embodiment, a plate body includes a plurality of holes for receiving anchors and/or anchor retaining devices. The plurality of holes are lined with, formed by or otherwise include a rigid port structure that provides at least a portion of the plurality of holes with a rigid contact portion for engagement by the anchors and/or retaining devices engaged to the plate. The rigid port structure may include a plurality of port elements positioned in respective ones of the plurality of holes. The rigid port structure may also include a bridging or linking element that interconnects the plurality of port elements so that a single port structure may be engaged to the plate to line, define or form at least two of the plurality of holes. The bridging element can be configured with a receptacle to receive a retaining device positioned between the at least two plate holes. The rigid port structure may be engaged along the upper or proximal surface of the plate body, the lower or distal surface of the plate body, or extend between the proximal and distal surfaces of the plate body.

It is also contemplated, however, that the port structure can be configured for positioning in a single hole in the plate body. In a further embodiment, the rigid port structure includes an end flange that can be outwardly deflected or deformed to engage the port structure to the plate. In another embodiment, the rigid port structure includes distal and proximal outwardly extending flanges and a body between the flanges that lines the corresponding hole of the plate with the plate extending between the flanges.

Many objects and benefits of the invention will become apparent upon consideration of the following written description of the invention, together with the accompanying Figures.

DETAILED DESCRIPTION OF THE ILLUSTRATED EMBODIMENTS

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 1A:
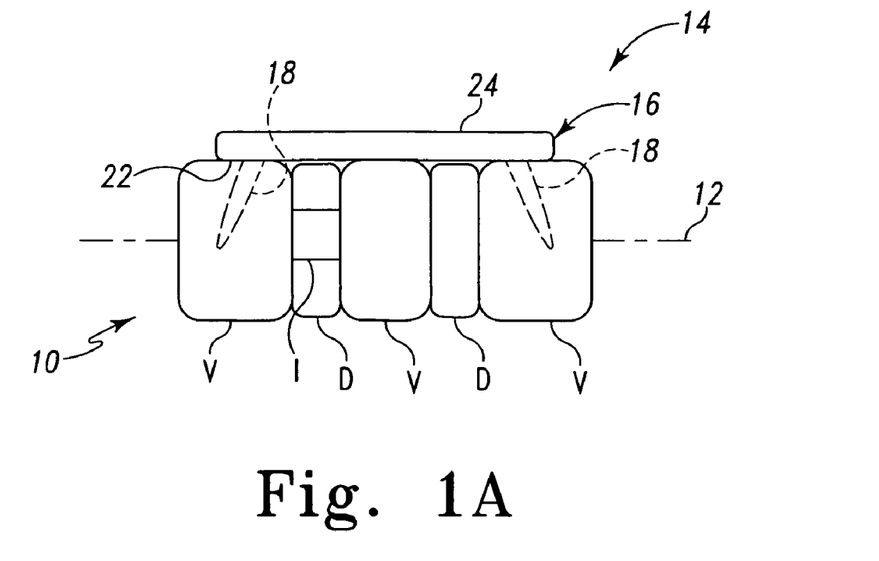
FIGS. 1A and 1B are diagrammatic side and plan views, respectively, of a spinal column segment with plating systems attached thereto.

In FIG. 1A there is shown a diagram of a spinal column segment 10 including a number of vertebrae V extending along spinal column axis 12. Vertebrae V may comprise any one or combination of the sacral, lumbar, thoracic and cervical regions of the spine. Adjacent ones of the vertebrae V can be separated by a disc space D, and one or more of the disc spaces D may include one or more implants I therein. Implant I can be a fusion device, bone graft, artificial disc implant, or other suitable spacing device.

Figure 1B:
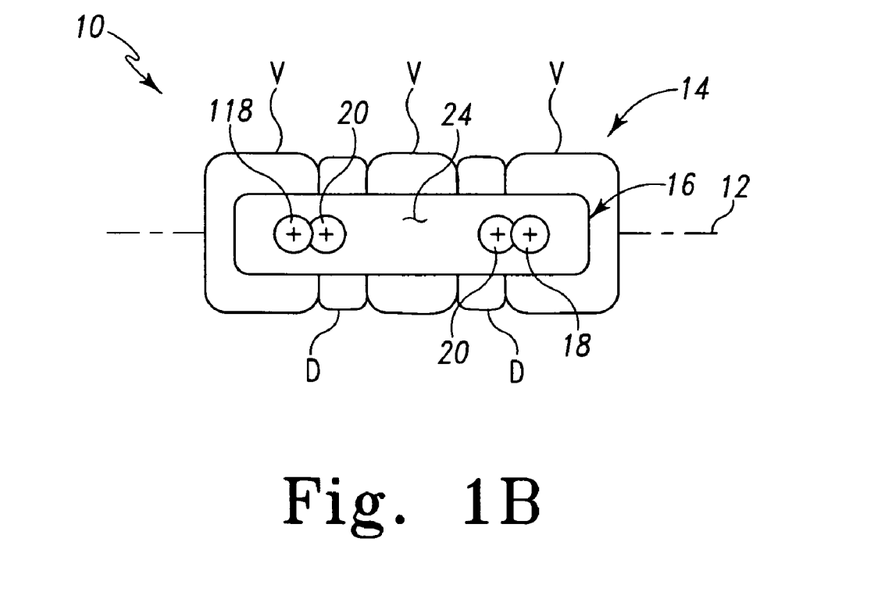

FIGS. 1A and 1B show a plating system 14 secured along vertebrae V. Plating system 14 may include one or more plates 16, anchors 18 securing the plate to one or more of the vertebrae V, and one or more optional retaining devices 20 to prevent the anchors 18 from backing out of the plate 16. Plate 16 includes a lower or distal surface 22 positionable along or adjacent the vertebrae V and an opposite upper or proximal surface 24. One or more holes may be provided between the distal and proximal surfaces 22, 24 to receive anchors 18 and/or retaining devices 20.

Plating system 14 may be employed along any one or combination of the anterior, anterior-oblique, lateral, postero-lateral, or posterior surfaces of the spinal column. Plating system 14 may be engaged to the anterior body structure of the respective vertebrae V, or to the posterior elements of the vertebrae V, such as the pedicles or spinous processes. In addition, the plating system may include multiple plates employed along the same or different vertebrae and vertebral levels, and in the same or different approaches to the vertebral levels.

Figure 2:
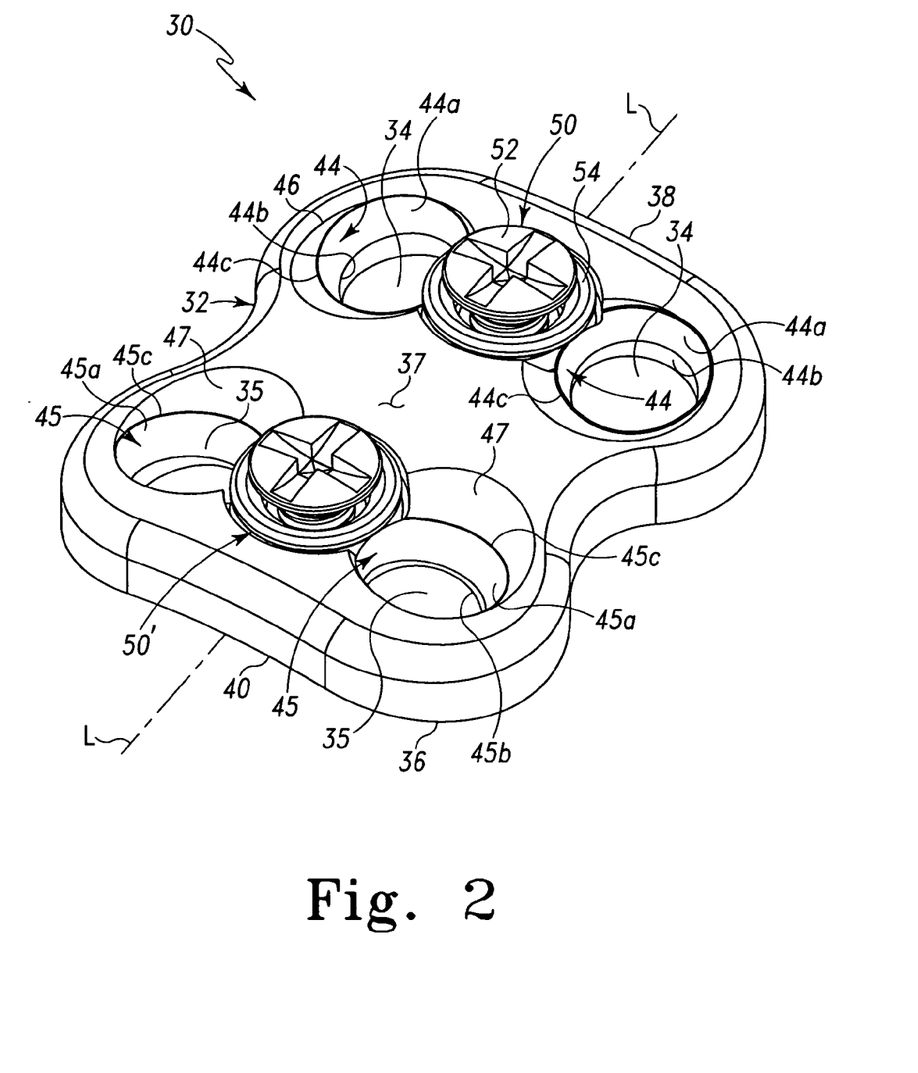
FIG. 2 is a top perspective view of one embodiment plate of the plating systems of FIG. 1.

One embodiment of a bone plate 30 comprising plating system 14 is shown in FIG. 2. Plate 30 include an elongated body 32 having at least one hole 34, 35 at each end thereof extending between and opening at a distal surface 36 and a proximal surface 37. Body 32 further extends between a first end 38 and a second end 40. The length of plate 30 between ends 38, 40 can be sized to extend along at least two vertebrae. It is further contemplated that the length can be sized to extend along three, four or five or more vertebrae.

Body 32 can be comprised of a first material, such as a polymer, so that it is non-rigid. This non-rigid structure further defines each of the holes 34, 35. Holes 34, 35 can each or selectively include a rigid insert providing a port structure 44, 45 in the respective holes 34, 35 such that the port structure is more rigid than the body 32 of plate 30. Accordingly, anchors positioned in holes 34, 35 at least partially contact the respective port structure 44, 45 and resist or prevent deformation of body 32 around holes 34, 35.

Port structure 44 can include a proximal portion 44a defining a concave recess or bowl-like shape and a distal portion 44b forming a cylindrical shape that is linear in the distal and proximal directions. Distal portion 44b opens at the distal surface 36 of plate 30, and proximal portion 44a extends proximally from distal portion 44b to a proximal edge 44c. Similarly, port structure 45 can include a proximal portion 45a defining concave recess or bowl-like shape and a distal portion 45b forming a cylindrical shape. Distal portion 45b opens at the distal surface 36 of plate 30, and proximal portion 45a extends proximally from distal portion 45b to a proximal edge 45c. Port structures 44, 45 can be circular in shape or elongated to form a slot to allow positioning of the anchor at various locations therealong. The port structures 44, 45 can be configured to engage the anchor to prevent pivoting of the anchor when seated in the port structure, or can allow pivoting of the anchor when positioned and seated in the port structure.

Edges 44c, 45c are in communication with and adjacent to proximal recessed surfaces 46, 47 in the proximal surface 37 of plate 30. Proximal recessed surfaces 46, 47 can facilitate guiding of the anchor into the respective hole 34, 35 in a desired approach while minimizing tissue retraction at the first and second ends 38, 40. The underside of the head of anchor 18 can be positioned or seated in contact with proximal portion 44a, 45a in a concave-convex relationship. As the anchor is tightened into contact with proximal portion 44a, 45a, deformation and pull-through of the plate relative to the anchor is resisted or prevented by the rigid interface with the respective port structure 44, 45. In addition, distal portion 44b, 45b can provide a rigid interface about the hole that is contacted by the anchor as the anchor pivots relative to the plate, resisting deformation of the body 32 about the respective holes 34, 35.

Holes 34, 35 are situated through the plate so that at least one anchor is positionable therethrough to engage at least one of the vertebrae V. In the illustrated embodiment, a pair of holes 34 are situated in a side-by-side arrangement on opposite sides of longitudinal axis L to receive two anchors to engage the underlying vertebra, and the other end of plate 30 includes a pair of holes 35 similarly situated to receive anchors to engage another vertebra. Other embodiments contemplate other hole arrangements at the ends of the plate, including three, four or five or more holes. The holes 34 can be aligned axially; including one hole aligned axially and another offset axially; arranged in a holes pattern including triangular, diamond, square, circular, and random patterns, for example.

The plate also can be divided into vertebral level or nodes with a serpentine appearance along its outer lateral edges as shown in FIG. 2. Other embodiments contemplate the plate includes linear edges, or edges that taper to form a trapezoid or triangular shape. The transitions between adjacent edges and surfaces can be smooth and rounded to reduce or prevent irritation of tissue in contact therewith. The plate can have a width to accommodate multiple, lateral anchors or a smaller width to reduce its profile and provide a single hole for each vertebra. In still other embodiments, the distal surface 36 can be concavely curved along and/or transversely to longitudinal axis L to fit along the vertebral surfaces. Other embodiments contemplate that plate 30 includes a distal surface 36 that is convexly curved along and/or transversely to longitudinal axis L. Proximal surface 37 can be arranged in parallel with distal surface 36 to provide a uniform thickness or in non-parallel relationships with distal surface 36 to provide varying plate thickness along the width and/or length of plate 30. Distal surface 36 can be provided with a textured profile, ridges, ribs, flanges or other structure to enhance or provide engagement with the adjacent bony tissue in contact with distal surface 36. The portion of body 32 between vertebrae V can include a window to facilitate viewing of the disc space, or include a construct extending from distal surface 36 that is positionable in the disc space to support the adjacent vertebra and/or carry graft or fusion promoting material.

The body 32 of plate 30 can be constructed, primarily, of a radiolucent material, such as a polymer based resin. In one embodiment, body 32 is constructed substantially from a polyetheretherketone (PEEK) high temperature thermoplastic commercially available by Invibio Biomaterial Solutions of Lancashire, UK under the tradename PEEK-OPTIMA. Using such material, conventional imaging of bony structures associated with the plate 30, such as with X-ray, computerized axial tomography (CAT) scanning, or magnetic resonance imaging (MRI) is improved due to the lack of imaging artifacts and scatter compared to that generated from metallic implants. Also, polymers such as PEEK will bow, flex and bend to a limited degree. This flexibility can be used to provide better healing/fusion between the fractured bone or fused vertebral bodies by allowing increased relative motion and avoiding stress shielding. Plate 31 can further include one or more bone growth or fusion-promoting elements, such as bone, bone morphogenetic protein (BMP), demineralized bone matrix (DBM), LIM mineralization proteins (LMP), osteogenic pastes, and so forth.

The plate embodiments may also provide a device 20 for retaining anchors positioned in holes 34, 35 to prevent backout or loosening of the anchor relative to the plate and bone structure to which the anchors are engaged. FIG. 1 illustrates one embodiment retaining device 50 including a fastener 52 and a retaining member 54 extending outwardly from fastener 52. Fastener 52 can be engaged to plate body 32 between holes 34. A second retaining device 50' is provided between holes 35 of plate body 32. In this arrangement, a single retaining device may be disposed between the two holes 34 or 35 and configured to lock or retain anchors positioned within holes 34 or 35. Fastener 52 can be, for example, a machine screw that engages with threads in the plate body 32, or can be a self-tapping screw that cuts through the plate body 32 as it is advanced therein. Other embodiments contemplate that fastener 52 could be a rivet, post, clamp or other device that engages plate body 32. Retaining member 54 can be a washer that projects radially outwardly sufficiently to overlap the holes 34 or holes 35 and/or contact the head of the anchors seated in the respective holes. Retaining member 54 can also be integral with fastener 52 to provide a flange or head that contacts the anchors and/or overlaps the screw holes.

Other types of retaining devices include a rotatable disk, lever, or rivet shaped to selectively allow one or more anchors to be inserted and then the retaining device is moved to a position to retain the inserted anchor; a deformable portion (e.g., a washer, clip, C-ring or tab) that selectively allows one or more anchors be inserted and then the retaining device is deformed to a retaining position; strap/tie mechanisms that can be used to selectively tie down one or more anchors; and a sliding member for moving between different positions to selectively allow one or more anchors to be inserted and then the member is slid into a retaining position relative to the inserted anchors.

Figure 3:
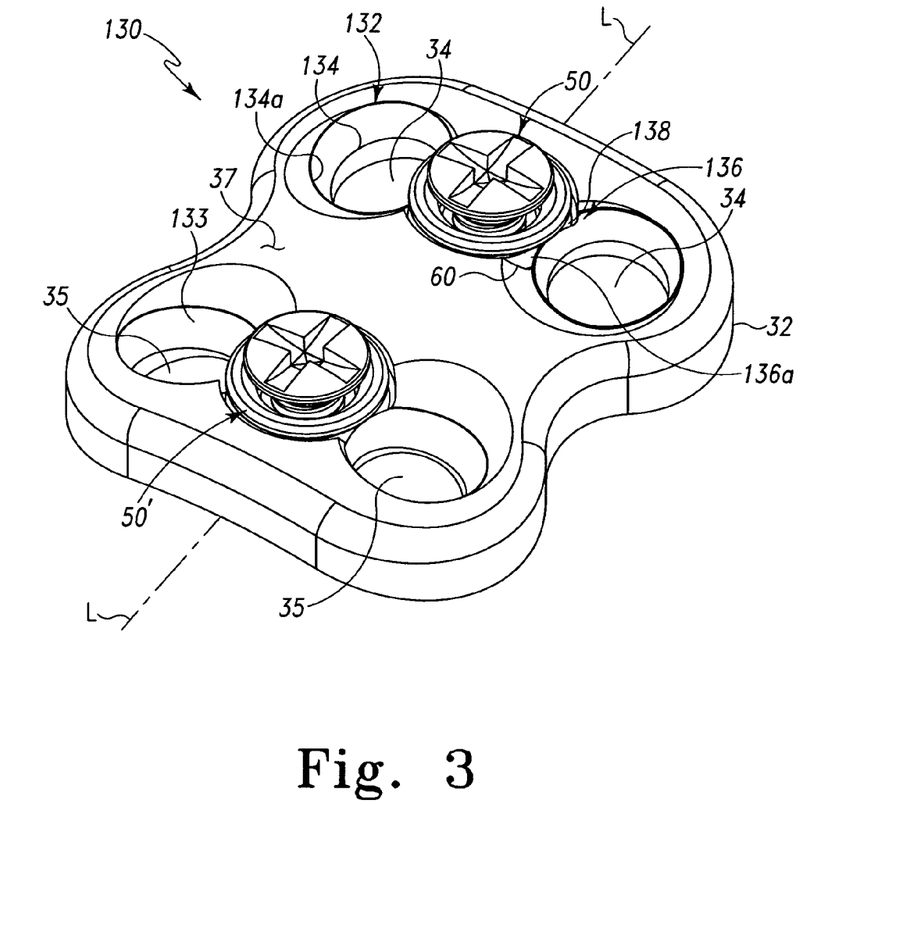
FIG. 3 is a top perspective view of another embodiment plate of the plating systems of FIG. 1.

Referring now to FIG. 3 there is shown another embodiment plate 130 that can be identical to plate 30 discussed above, but includes another embodiment port structure 132 positioned in holes 34. An identical port structure 133 can be positioned in holes 35 as shown, or any other port structure embodiment discussed herein. Port structure 132 can include a first port element 134 and a second port element 136. Port elements 134, 136 can each be identical to port structures 44, 45 discussed above. However, the proximal ends 134a, 136a are connected to one another with a bridging or linking element 138 extending trans-axially across longitudinal axis L. Linking element 138 can include an aperture (not shown) to allow passage of and engagement of fastener 52 of retaining devices 50, 50' thereto. Linking element 138 can be located in a recess 60 extending between holes 34 that is formed in proximal surface 37 of body 32.

Figure 4:
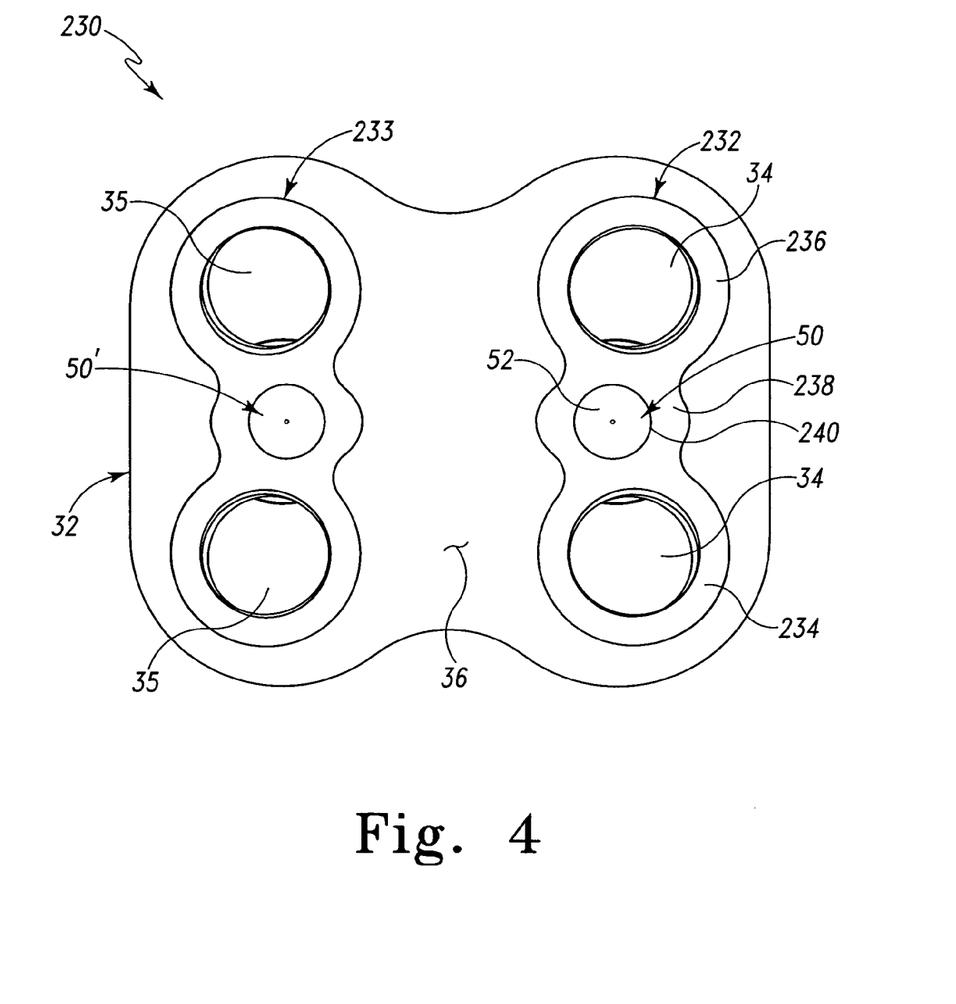
FIG. 4 is a bottom plan view of another embodiment plate of the plating systems of FIG. 1.
Figure 5:
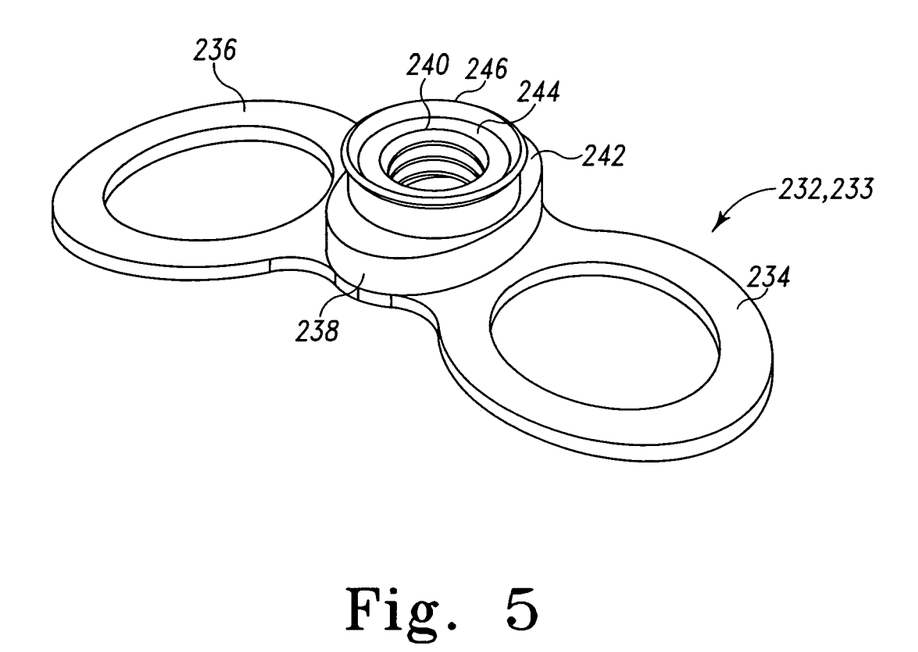
FIG. 5 is a perspective view of a rigid port structure of the plate of FIG. 4.
Figure 6:
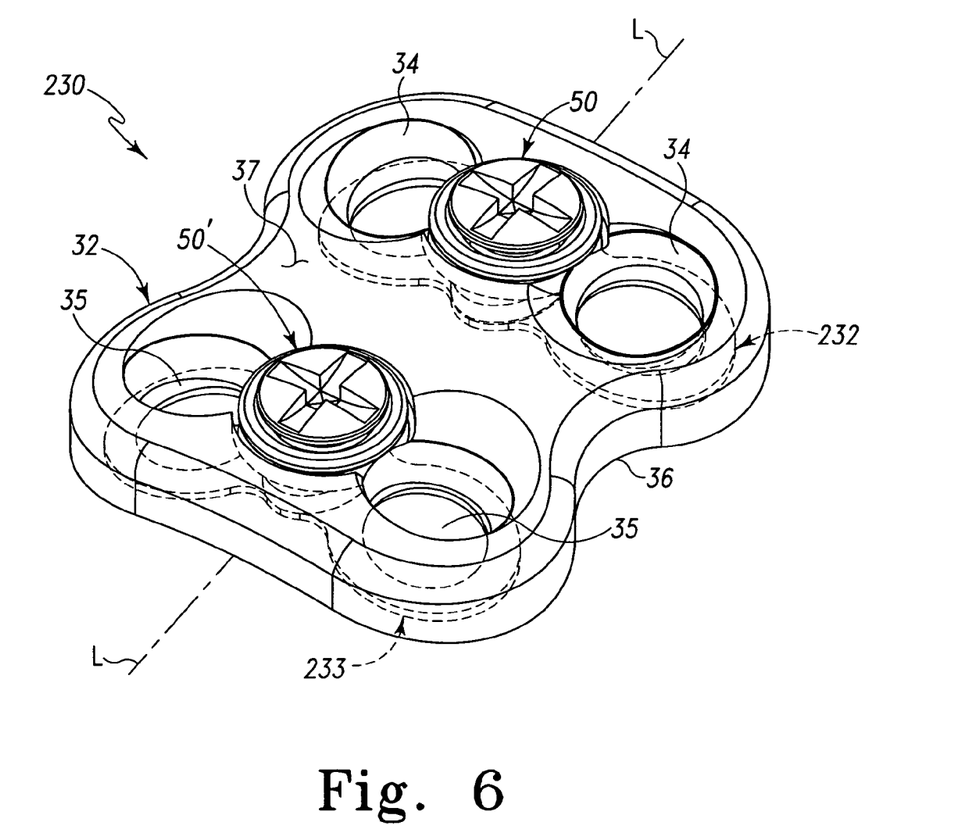
FIG. 6 is a top perspective view of the plate of FIG. 4.

Referring now to FIGS. 4-6 there is shown another embodiment plate 230 that can be identical to plate 30 discussed above, but includes another embodiment port structure 232 positioned in holes 34. An identical port structure 233 can be positioned in holes 35 as shown, or any other port structure embodiment discussed herein. Port structure 232 can include a first port element 234 and a second port element 236. Port elements 234, 236 can be connected to one another with a bridging or linking element 238 extending trans-axially across longitudinal axis L.

Port elements 234, 236 each include a ring-like shape with circular through-hole extending therethrough that is aligned with the respective holes 34, 35 of plate body 32 adjacent distal surface 36. Linking element 238 includes a distal base 242 along a distal portion thereof and a proximal receptacle 244 extending proximally from base 242. Receptacle 244 includes a central aperture 240 that opens proximally and distally therethrough. Aperture 240 can be internally threaded to receive fastener 52 therein. Receptacle 244 can further include a proximal flange 246 that can extend radially outwardly from aperture 240 to facilitate attachment of port structure 240 to plate body 232 with the plate body sandwiched between flange 246 and base 242. In addition, base 242 can be non-circular or elongated in at least one direction, such as along longitudinal axis L as shown, to resist rotation of port structure 232 relative to plate body 32.

Figure 7:
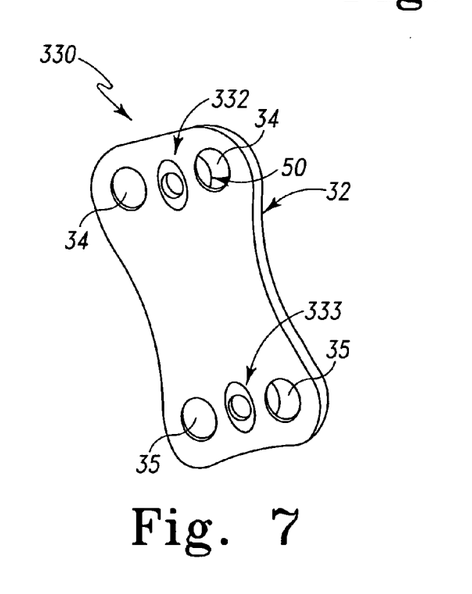
FIG. 7 is a bottom perspective view of another embodiment plate of the plating systems of FIG. 1.
Figure 8:
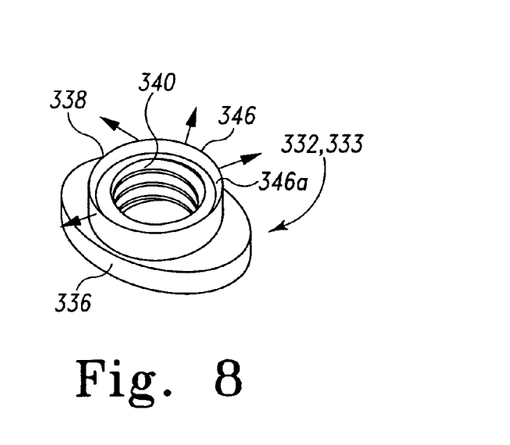
FIG. 8 is a top perspective view of a rigid port structure of the plate of FIG. 7 before attachment to the plate.

Referring now to FIGS. 7-8, there is shown another embodiment plate 330. Plate 330 can be identical to plate 30, and like elements are designated with the same reference numerals. Plate 330 includes a port structure 332 for a retaining device that is centrally positioned between hole pairs 34 and a second port structure 333 positioned between hole pairs 35. Port structures 332, 333 each include a base portion 336 and a receptacle 338 extending proximally from base portion 336. Receptacle 338 includes a central aperture 340 that opens proximally and distally therethrough. Aperture 340 can be internally threaded to receive fastener 52 therein.

Receptacle 338 can further include a proximal retaining flange 346 that can be deformed to extend radially outwardly from aperture 340 to facilitate attachment or staking of port structure 332, 333 to plate body 32 with the plate body sandwiched between flange 346 and base 336. In the illustrated embodiment, flange 346 includes a tapered wall surface 346a along the surface adjacent aperture 340. A ball-shaped member of a forming instrument can be positioned adjacent this tapered surface 346a and pushed there against to bend or roll flange 346 radially outwardly against or adjacent to proximal surface of the plate body 32. In addition, base 336 can be non-circular or elongated in at least one direction, such as along longitudinal axis L as shown, to resist rotation of port structure 332, 333 relative to plate body 32.

Figure 9:
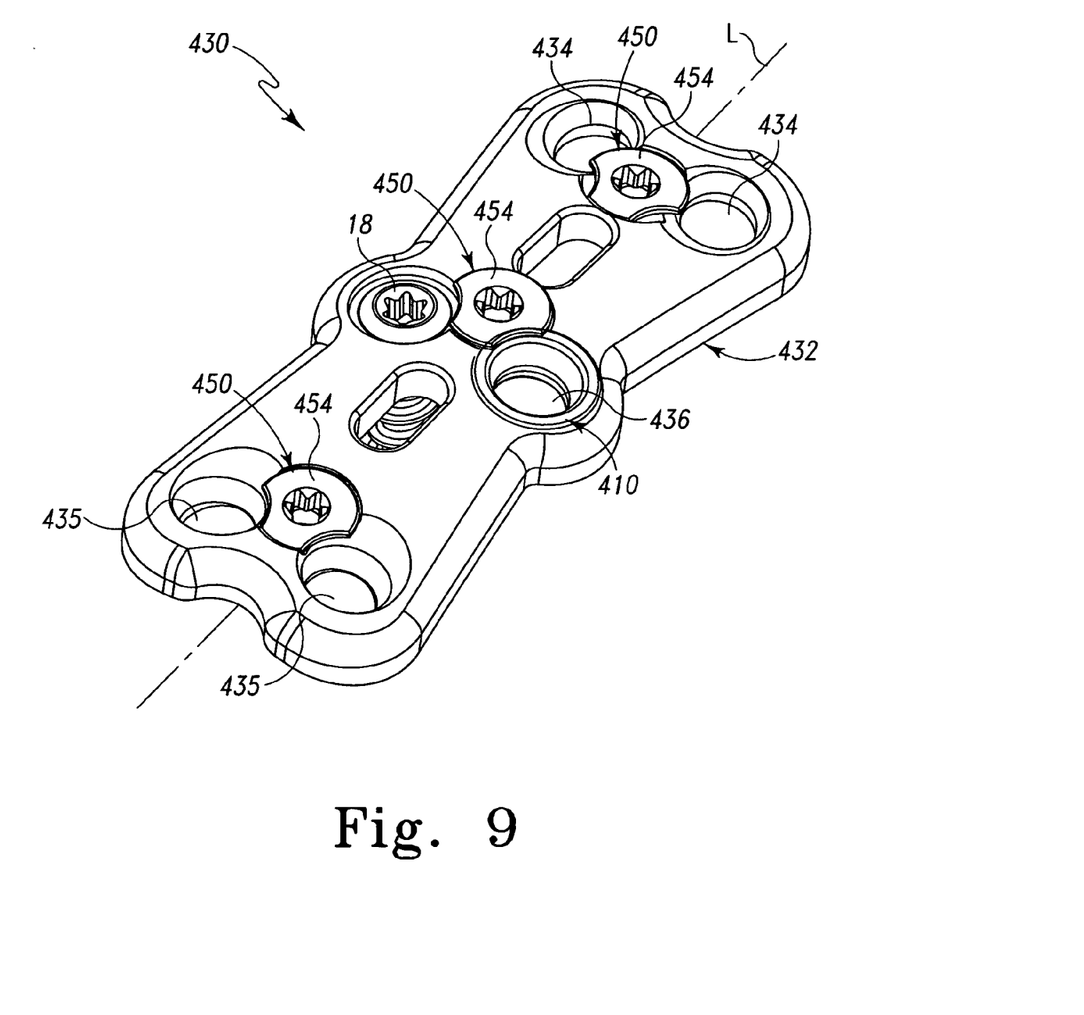
FIG. 9 is a top perspective view of another embodiment plate comprising the plating systems of FIG. 1.
Figure 10:
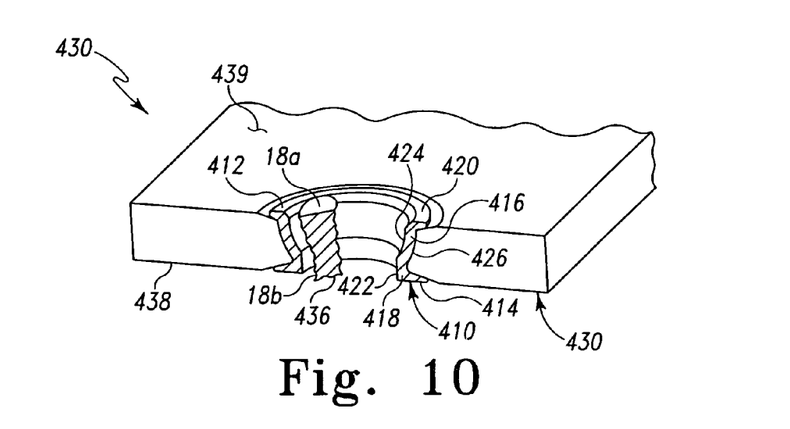
FIG. 10 is a sectional view of a rigid port structure of the plate of FIG. 9 and an anchor in the port structure.

Referring now to FIGS. 9-10, there is shown another embodiment plate 430 with another embodiment port structure 410. Plate 430 includes a plate body 432 with a length along longitudinal axis L to extend along three vertebrae, although application with single level and other multi-level plates are also contemplated. Plate 430 includes a first hole pair 434 adjacent a first end and a second hole pair 435 adjacent a second end. A third hole pair 436 is provided about mid-length along plate 430. Anchor 18 in the form of a bone screw is positioned in one of the holes of hole pair 436, it being understood that the other holes can be provided with an anchor 18 situated therein to secure the plate to the underlying vertebral body.

Plate 430 further includes a number of retaining devices 450 secured thereto. Respective ones of the retaining devices 450 are positioned between respective ones of the hole pairs 434, 435, 436. Retaining devices 450 include a proximal flanged element 454 and a distal fastener portion (not shown) to attach to plate body 432. Flanged elements 454 can include a pair of cutouts or recesses thereabout that are positionable adjacent respective ones of the holes of a respective adjacent hole pair to allow anchor insertion into the holes. The retaining device is thereafter rotatable so that the flanged element 454 overlaps the respective adjacent holes and blocks or prevents the anchor from backing out the plate hole.

Port structure 410 includes a proximal flange 412 and a distal flange 414 and a body 416 extending therebetween. Proximal flange is located adjacent proximal surface 439 of plate body 432 and distal flange 414 is located adjacent distal surface 438. Body 416 includes a distal portion 418 and a proximal portion 420. Distal portion 418 includes a linear inner surface 422 defining a cylindrical shape to receive a shaft 18b of anchor 18 therethrough. Proximal portion 420 includes a concavely curved inner surface 424 that engages the underside of the head 18a of anchor 18. Body 416 can include a convexly curved outer surface 426 extending between flanges 412, 414. Plate body 432 is positioned between flanges 412, 414, and the outer surface 426 and flanges 412, 414 prevent port structure 410 from being pushed distally through plate body 432 as anchor 18 is seated thereagainst.

The port structures discussed herein may be made from any suitable biocompatible metal or metal alloy, including titanium, stainless steel, and aluminum; ceramic material; polymers and other plastics or elastomers that exhibit a rigidity greater than that of the plate material. The port structures can be swaged to the desired shape or formed with any suitable process or technique. The port structures provide an improved interface for the anchors and/or anchor retaining devices with the plate body.

Various techniques for securing the port structure to the plate are contemplated. At least a portion of the part structure may be embedded in the plate body to engage the port structure thereto. The port structures may be pressed into form fitting engagement with the plate body. The port structure can include mechanical structures or fasteners that positively engage the plate. The plate can be over-molded or formed about the port structure. The port structure can also be positioned in a plate opening or recess and deformed to positively engage the plate body.

Although only a few exemplary embodiments of this invention have been described in detail above, those skilled in the art will readily appreciate that many modifications are possible in the exemplary embodiments without materially departing from the novel teachings and advantages of this invention. Also, features illustrated and discussed above with respect to some embodiments can be combined with features illustrated and discussed above with respect to other embodiments. Accordingly, all such modifications are intended to be included within the scope of this invention.

What is claimed is:

1. A plating system for stabilizing a spinal column segment, comprising:
    a plate body extending between a first end and an opposite second end along a longitudinal axis, said plate body including a distal surface positionable adjacent the spinal column segment and an opposite proximal surface, said plate body further including at least two holes extending between said distal and proximal surfaces, said at least two holes being located on opposite sides of said longitudinal axis; and
    a port structure positioned about at least a portion of each of said at least two holes, said port structure including a distal portion in each of said at least two holes adjacent said distal surface of said plate body and a proximal portion in each of said at least two holes adjacent said proximal surface of said plate body, said distal portion including an inner surface defining a cylindrically shaped portion of each of said at least two holes and said proximal portion including an inner surface defining a concave recessed portion of each of said at least two holes for receiving a head of an anchor therein, wherein said port structure includes a linking element extending between said proximal portions of said port structure on said proximal surface of said plate body and a receptacle extending through said linking element into said plate body at a location between said at least two holes for receiving a retaining device.

2. The plating system of claim 1, wherein said plate body is made of a first material and said port structure is made of a second material and is more rigid than said plate body.

3. The plating system of claim 2, wherein said first material is PEEK and said second material is a metal or metal alloy.

4. The plating system of claim 1, further comprising said anchor positioned in said port structure with said head of said anchor in contact with said proximal portion and a shaft of said anchor extending through said distal portion.

5. The plating system of claim 1, wherein said port structure includes a distal flange and a proximal flange and a body extending in at least one of said at least two holes between said distal and proximal flanges, said body including said inner surfaces of said distal and proximal portions therealong.

6. The plating system of claim 5, wherein said body of said port structure includes an outer surface defining a convexly curved shape between said proximal and distal flanges and said proximal and distal flanges project outwardly from said outer surface.

7. The plating system of claim 6, wherein said proximal flange is positioned in contact with said proximal surface of said plate body and said distal flange is positioned in contact with said distal surface of said plate body.

8. The plating system of claim 5, wherein said proximal flange is positioned in contact with said proximal surface of said plate body and said distal flange is positioned in contact with said distal surface of said plate body and said plate body extends between said proximal and distal flanges.

9. A plating system for stabilizing a spinal column segment, comprising:
    a plate body extending between a first end and an opposite second end along a longitudinal axis, said plate body including a distal surface positionable adjacent the spinal column segment and an opposite proximal surface, said plate body further including at least one hole extending between said distal and proximal surfaces; and
    a port structure including a ring element positioned around said at least one hole for receiving a bone anchor, said port structure including a linking member extending from said ring element across said longitudinal axis on said distal surface of said plate body and said port structure further includes a receptacle extending proximally from said linking member to a flange adjacent said proximal surface of said plate body, wherein said flange is deformed from a first position extending proximally from said receptacle to a second position extending radially outwardly from said receptacle into engagement with said plate body for receiving a retaining device.

10. The plating system of claim 9, wherein said receptacle includes an aperture opening proximally through said flange.

11. The system of claim 10, wherein said aperture is internally threaded along said receptacle.

12. The plating system of claim 11, further comprising said retaining device threadingly engaged in said receptacle.

13. The plating system of claim 12, further comprising a pair of holes positioned on opposite sides of said at least one hole, said pair of holes each including a ring element of said port structure extending thereabout and said receptacle is located between said ring elements.

14. The plating system of claim 9, wherein said linking element of said port structure includes a flange extending outwardly from said receptacle.

15. The plating system of claim 14, wherein said flange includes a non-circular shape.

16. A plating system for stabilizing a spinal column segment, comprising:
    a plate body extending between a first end and an opposite second end along a longitudinal axis, said plate body including a distal surface positionable adjacent the spinal column segment and an opposite proximal surface, said plate body further including at least two holes extending between said distal and proximal surfaces; and a port structure including first and second port elements positioned around a portion of respective ones of said at least two holes for receiving bone anchors between said distal and proximal surfaces and a linking element extending on said distal surface across said longitudinal axis of said plate body and a receptacle between said first and second port elements for receiving a retaining device, said receptacle extending proximally from said linking element through said plate body, said linking element extending between and connecting said first and second port elements to one another.

17. The plating system of claim 16, wherein said first and second port elements each include:

a distal portion adjacent said distal surface of said plate body and a proximal portion adjacent said proximal surface of said plate body, said distal portion including an inner surface defining a cylindrically shaped portion of said respective one of said at least holes and said proximal portion including an inner surface defining a concave recessed portion of said respective one of said at least two holes.

18. The plating system of claim 16, further comprising said retaining device engaged to said receptacle and overlapping said at least two holes.

19. The plating system of claim 16, wherein said first and second port elements of said port structure each include a ring-shaped body with a through-hole aligned with a respective one of said at least two holes of said plate adjacent said distal surface of said plate body.

20. The plating system of claim 16, wherein said receptacle includes a central, proximally opening aperture to receive said retaining device between said at least two holes of said plate body.

21. The plating system of claim 20, wherein said receptacle is threaded about said aperture.

22. The system of claim 20, wherein said base portion includes a non-circular shape and said receptacle includes a circular cylindrical shape extending proximally from said base portion to a proximal flange, said flange extending radially outwardly from said receptacle to sandwich said plate body between said flange and said base portion.

23. The plating system of claim 16, wherein said plate body is made of a first material and said port structure is made of a second material and is more rigid than said plate body.

24. The plating system of claim 23, wherein said first material is PEEK and said second material is a metal or metal alloy.

25. The plating system of claim 16, further comprising anchors positioned in said at least two holes of said plate body with said anchors extending through respective ones of said port elements.

26. The plating system of claim 25, further comprising said retaining device engaged to said linking element between said anchors in overlapping relation with said at least two holes.

27. A method for forming a spinal plate, comprising:

forming a body of the plate from a non-rigid material with the body extending along a longitudinal axis between a first end and an opposite second end thereof, the body further having a distal surface positionable adjacent a spinal column and an opposite proximal surface and at least two holes extending between the distal and proximal surfaces wherein the at least two holes are located on opposite sides of the longitudinal axis; and embedding a rigid port structure in the body of the plate with at least one of two port elements of the port structure aligned with a respective one of the at least two holes for receiving bone anchors and with the port elements linked to one another with a bridging element on said distal surface of said body of said plate wherein the port structure includes a receptacle extending from bridging element between the at least two holes for receiving a retaining device.

28. The method of claim 27, wherein embedding the rigid port structure includes positioning the bridging element between the at least two holes.

29. The method of claim 28, further comprising securing the retaining device to the bridging element.

30. The method of claim 27, wherein the bridging element includes a base adjacent the distal surface of the body and the receptacle extending proximally from the base, and further comprising securing the retaining device in the receptacle in overlapping relations with the at least two holes.

31. The method of claim 27, further comprising positioning the anchor in one of the at least two holes in contact with the respective port element.

* * * * *